(12) United States Patent
Misholi et al.

(10) Patent No.: US 7,032,463 B2
(45) Date of Patent: *Apr. 25, 2006

(54) RESPIRATORY FLOW SENSOR

(75) Inventors: Boaz Misholi, New York, NY (US);
Mark Shahar, Holon (IL); Sajed Haj-Yahya, Taybe (IL)

(73) Assignee: Versamed Medical Systems Ltd., Kadima (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/960,276

(22) Filed: Oct. 8, 2004

(65) Prior Publication Data

US 2005/0109122 A1    May 26, 2005

Related U.S. Application Data

(63) Continuation of application No. 10/200,764, filed on Jul. 24, 2002, now Pat. No. 6,802,225.

(51) Int. Cl.
*G01F 1/37* (2006.01)

(52) U.S. Cl. .................................. 73/861.52; 73/861.63

(58) Field of Classification Search .................... None
See application file for complete search history.

(56) References Cited

U.S. PATENT DOCUMENTS

| | | | | |
|---|---|---|---|---|
| 4,932,269 | A * | 6/1990 | Cammarata et al. | 73/861.61 |
| 5,088,332 | A * | 2/1992 | Merilainen et al. | 73/861.65 |
| 5,379,650 | A * | 1/1995 | Kofoed et al. | 73/861.52 |
| 5,789,660 | A * | 8/1998 | Kofoed et al. | 73/23.2 |
| 5,913,249 | A * | 6/1999 | Weckstrom | 73/861.52 |
| 5,979,247 | A * | 11/1999 | Kizawa | 73/861.53 |
| 6,203,502 | B1 * | 3/2001 | Hilgendorf et al. | 600/538 |
| 6,312,389 | B1 * | 11/2001 | Kofoed et al. | 600/532 |
| 6,802,225 | B1 * | 10/2004 | Shahar et al. | 73/861.52 |

* cited by examiner

*Primary Examiner*—Harshad Patel
(74) *Attorney, Agent, or Firm*—AlphaPatent Associates Ltd.; Daniel J. Swirsky

(57) ABSTRACT

A respiratory tract differential-pressure flow sensor, including a tube having a distal end that is insertable into a respiratory tract, an interfering body disposed within the tube proximal to the distal end and having a first edge facing one end of the tube and a second edge facing away from the end, the interfering body extending across the diameter of the tube, a first pressure sensing port operative to sense an air pressure, the first port being disposed in the first edge not abutting the wall of the tube, and a second pressure sensing port operative to sense an air pressure, the second port being disposed in the second edge not abutting the wall of the tube, where either of the edges is inclined inwardly towards the axis of the interfering body extending across the diameter of the tube.

1 Claim, 6 Drawing Sheets

RESPIRATORY FLOW SENSOR

CROSS-REFERENCE TO RELATED APPLICATIONS

The present application is a continuation of U.S. patent application Ser. No. 10/200,764, filed Jul. 24, 2002, now U.S. Pat. No. 6,802,225 entitled "Respiratory Flow Sensor," and incorporated herein by reference in its entirety.

FIELD AND BACKGROUND OF THE INVENTION

The present invention relates generally to the field of medical devices and specifically to medical devices that are designed to monitor the respiratory characteristics of patient breathing, especially for those patients who are attached to mechanical ventilators.

Persons exhibiting acute or chronic respiratory failure, for example due to pulmonary infection or trauma, often require artificial ventilatory support and may therefore be connected, by means of flexible plastic ventilation tubing, to a mechanical ventilator. Correct functioning of such a ventilator entails continuous, accurate and reliable monitoring, by the ventilator, of airflow characteristics within the connecting plastic tubing. Such monitoring is often achieved by means of a gas-flow sensor interposed within the plastic ventilation tubing connecting the patient to the ventilator.

It will be well known to those familiar with the art that many mechanical ventilators utilize a flow sensor fashioned in the form of a bore of cylindrical tubing containing within it a strut, also known as an interfering body, in a manner which facilitates differential pressure measurements, at either end of the strut, that are proportional to the flow rate of the respiratory gases that pass through the sensor. Such a flow sensor is hereinafter referred to as a differential-pressure flow sensor, and is described in more detail below.

A differential-pressure flow sensor typically is comprised of a hollow cylindrical body having a bore, which can be connected between a ventilator and a patient. The differential-pressure flow sensor utilizes an aerodynamic strut that is disposed within the cylindrical bore of the sensor to create a drop in the pressure of the respiratory gases flowing through the sensor. The strut extends across the entire diameter of the bore of the flow sensor and bisects the circular bore of the sensor. The width of the strut is less than the diameter of the bore and the longitudinal length of the strut is less than the length of the bore. Further, the geometric cross section of the strut is symmetrical to the flow of respiratory gases flowing through the sensor in either direction, and has a generally elliptical cross section. The aerodynamic design of the strut preserves the laminar nature of airflow through the cylindrical bore as the air passes around the strut, such that airflow turbulence is minimal or absent within the flow sensor.

The aerodynamic strut has longitudinally exposed edge portions, such that when the differential-pressure flow sensor is interposed between a patient and a ventilator one edge portion is closer to the patient and the other edge portion is closer to the ventilator. Each of the edge portions of the aerodynamic strut contains a semicircular groove running the full height of the edge, that is, parallel to the short axis of the cylindrical body and extending from the inner surface of the cylindrical body on one side to the inner surface of the cylindrical body on the opposite side of the cylindrical body. One end of each groove is in continuity with a circular lumen within the wall of the cylindrical body. This circular lumen is thus located at the intersection between the inner surface of the cylindrical body and the edge portion of the aerodynamic strut. The circular lumen extends through the wall of the cylindrical body. On the outer surface of the cylindrical body this lumen receives tubing, which runs from the differential-pressure flow sensor to a pressure transducer, typically located within the mechanical ventilator.

The differential pressure measured by the flow sensor is due to the restriction to flow caused by the presence of the strut within the bore of the sensor. The drop in pressure is measured relatively between the groove in the first edge portion of the aerodynamic strut and the groove in the second edge portion of the aerodynamic strut. For example, when respiratory gases are flowing through the flow sensor from the first end to the second end, a high-pressure zone, also referred to as an area of static pressure, is created immediately adjacent to the first edge of the strut and a low-pressure zone, also referred to as an area of dynamic pressure, is created immediately adjacent to the second edge of the strut. The converse is true when the respiratory gases are flowing from the second end of the sensor toward the first end of the sensor. It should be emphasized that in terms of the functioning of the differential-pressure flow sensor, the actual point at which pressure is measured, using the venturi principle, is at the circular lumen on the inner surface of the cylindrical body, and that this pressure measurement reflects the pressure along the length of the groove in the edge portion of the aerodynamic strut.

The relative pressures of the respiratory gases flowing through the sensor are collected and conveyed to the pressure transducer through the circular lumens and the tubing connected thereto. The pressure transducer measures the received pressures, and the resultant data is then processed by a microprocessor so as to calculate the rate of gas flow through the differential-pressure flow sensor. This calculation is based on the principle that the drop in pressure across an obstruction in an airway is related to the square of the velocity of the fluids flowing through the airway. This principle is also true for the differential-pressure flow sensor. The general relationship between the flow velocity and the pressure drop as measured across the strut by the transducer is given by:

$$(\text{flow velocity})^2 \, \Delta P$$

where $\Delta P$ is the drop in pressure across the strut of the differential-pressure flow sensor. This relationship is unique for every unique flow sensor geometry and must be derived empirically. Accordingly, the plastic flow sensors that are used with a given ventilator and microprocessor are manufactured from the same molds and injection conditions so that the geometric variation between each flow sensor is negligible.

Determining the flow-to-pressure drop relationship is accomplished by forcing air through the differential-pressure flow sensor at predetermined flow rates and measuring the resulting changes in differential pressure across the strut through the lumens, so as to generate a set of data points. A high order linear equation is then fit to the data points. This equation closely follows the same general form as given above. Using this equation, a flow velocity for gases flowing through the differential-pressure flow sensor can be calculated from the differential pressures measured across the strut.

It is known, however, that standard differential-pressure flow sensors, as described above, suffer from several deficiencies. In particular, standard differential pressure flow sensors have been found to function unreliably in the presence of high humidity within the respiratory gasses flowing through the sensor. Humidification of the inspired respiratory gasses is often achieved by flowing the respiratory gasses through a water humidifier before the gasses pass through the flow sensor and into the patient. This is desirable so as to prevent drying of the patient's respiratory tract mucousa during prolonged periods of mechanical ventilation. Humidity may also be introduced into the respiratory gasses in the form of aerosolized medications, which are frequently administered to mechanically ventilated patients. Even without the introduction of external humidity, the naturally expired respiratory gasses from a patient's lungs are of higher humidity than the inspired gasses, thus increasing the humidity of airflow through the differential-pressure flow sensor.

As the humidity of the respiratory gasses increases, water condensation may occur on the inner surface of the respiratory tubing and the differential-pressure flow sensor. When such condensation occurs in the circular lumen in the inner wall of the flow sensor, at which site pressure measurements are sensed, water blocks the lumen, thus distorting the pressure measurements recorded by the differential-pressure flow sensor, and invalidating the resultant flow data. Furthermore, water that has previously condensed elsewhere along the length of the flexible respiratory tubing may flow into the flow sensor due to movement of the tubing, and cover the pressure sensing lumen. The propensity for the pressure sensing lumen to become blocked by water is exacerbated by the narrow gauge of the lumen and its connected tubing, which causes liquid to enter the tubing by means of capillary action.

Several different solutions have been developed in an attempt to overcome this deficiency of differential-pressure flow sensors. One alternative has been to insert a heating electrode into the flow sensor so as to heat the inner surface of the sensor and thereby prevent water condensation. This technique requires the addition of electrical wiring and machinery to the flow sensor and ventilator, thus increasing the cost and mechanical complexity of the sensor. A second alternative has been to try ensure that the sensor remains oriented in space in such a way that the pressure-sensing lumen is on the superior aspect of the cylindrical body, rather than the dependent aspect where condensed water will accumulate due to gravity. This alternative has proven to be impractical, as movement of the patient or the flexible respiratory tubing inevitably results in movement of the flow sensor, and thus movement of the accumulated water within the sensor, causing blockage of the pressure-sensing lumen.

There is therefore a need for, and it would be highly advantageous to have, a differential-pressure flow sensor that prevents condensation of water vapor in the pressure-sensing lumens of the sensor, and that prevents blockage of the pressure-sensing lumens by condensed water which may flow into the sensor from the respiratory tubing. It would be desirable for such a sensor to achieve these aims without the addition of electrical components to the sensor.

SUMMARY OF THE INVENTION

The invention is a differential-pressure gas flow sensor, for use in mechanical ventilators, wherein the shape of the aerodynamic strut, or interfering body, prevents the lumens at which the differential pressures are sensed from becoming obstructed by condensed water. Three unique characteristics of the shape of the interfering body, which prevent water blockage of the pressure-sensing lumen from occurring and which are points of novelty of the current invention, are:

1) For each edge portion, the pressure-sensing lumen is located-on the edge portion of the interfering body-distant from the inner surface, and closer to the central axis of symmetry, of the cylindrical body. Consequently, accumulation of condensed water in the dependant part of the sensor (along its inner surface) does not block the pressure-sensing lumen, which remains above the water level.
2) The walls of the interfering body slope convergently from the elliptical base of the interfering body towards its center, rather than being essentially parallel to each other. This unique shape of the interfering body results in airflow patterns around the interfering body which generate turbulent boundary layer flow patterns near the base of the interfering body, distant from the pressure-sensing lumens. As turbulent boundary layers encourage water condensation and precipitation, these processes occur primarily at the base of the interfering body, rather than at the pressure-sensing lumens.
3) Each edge portion of the interfering body slopes at an angle from the base of the interfering body to the location of the pressure-sensing lumen. Consequently, the leading edge of the interfering body (namely, the leading edge which faces towards the source of airflow) deflects the airflow along a flow vector oriented towards the pressure-sensing lumen on the opposite (trailing) edge portion in such a way as to flush condensed water out of the area of the pressure-sensing lumen.

In one acpect of the invention a differential-pressure flow sensor is provided, including a) an interfering body, having a first edge, disposed within a tube, the interfering body extending across the diameter of the tube, and b) a first pressure sensing port operative to sense an air pressure, the first port being disposed in the first edge not abutting the wall of the tube.

In another aspect of the present invention the first edge is inclined at an angle with respect to the axis of the interfering body extending across the diameter of the tube.

In another aspect of the present invention the angle is about 13 degrees.

In another aspect of the present invention the first edge is a leading edge with regard to a direction of airflow.

In another aspect of the present invention sides of the interfering body are convergent with each other along the diameter of the tube.

In another aspect of the present invention sides of the interfering body converge at an angle of about ten degrees with respect to the axis of the interfering body extending across the diameter of the tube.

In another aspect of the present invention sides of the interfering body are concave.

In another aspect of the present invention the pressure sensing port is disposed upon the first edge.

In another aspect of the present invention the pressure sensing port is recessed within the first edge.

In another aspect of the present invention the pressure sensing port has a diameter of about 1.54 millimeters.

In another aspect of the present invention the pressure sensing port is disposed in the first edge at about the midpoint of the first edge.

In another aspect of the present invention the tube is operative to hold a volume of liquid, and where the port is disposed in the first edge at a distance from a wall of the tube that is greater than a depth of the volume of liquid.

In another aspect of the present invention the interfering body is operative to disturb an airflow, the disturbed airflow including a boundary layer in proximity to the wall of the tube.

In another aspect of the present invention the boundary layer is turbulent.

In another aspect of the present invention the tube is Y-shaped.

In another aspect of the present invention the tube is respiratory tubing.

In another aspect of the present invention the tube is an endotracheal tube.

In another aspect of the present invention the interfering body has a second edge, and further includes c) a second pressure sensing port operative to sense an air pressure, the second port being disposed in the second edge not abutting the wall of the tube.

In another aspect of the present invention the second edge is a trailing edge with regard to a direction of airflow.

In another aspect of the present invention the first edge is operative to deflect an airflow along a vector directed towards the second pressure sensing port.

In another aspect of the present invention a method for measuring airflow is provided, including a) providing a differential-pressure flow sensor, the sensor including an edge and a pressure-sensing port, and b) deflecting an airflow from the edge along a vector directed towards the pressure-sensing port sufficient to remove liquid from the pressure-sensing port.

In another aspect of the present invention a method for measuring airflow through a tube is provided, including a) providing a differential-pressure flow sensor, the sensor including an interfering body, the interfering body being operative to disturb airflow through the tube, and b) disturbing the airflow through the tube around the interfering body, the disturbed airflow including a turbulent boundary layer in proximity to the wall of the tube.

In another aspect of the present invention a method for measuring airflow through a tube is provided, including a) providing a differential-pressure flow sensor, the sensor being operative to sense a pressure, and b) sensing a pressure at a location not abutting the wall of the tube.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a differential-pressure respiratory flow sensor for use in a mechanical ventilator.

The principles and operation of a differential-pressure respiratory flow sensor, according to the present invention, may be better understood with reference to the drawings and the accompanying description.

Figure 1:
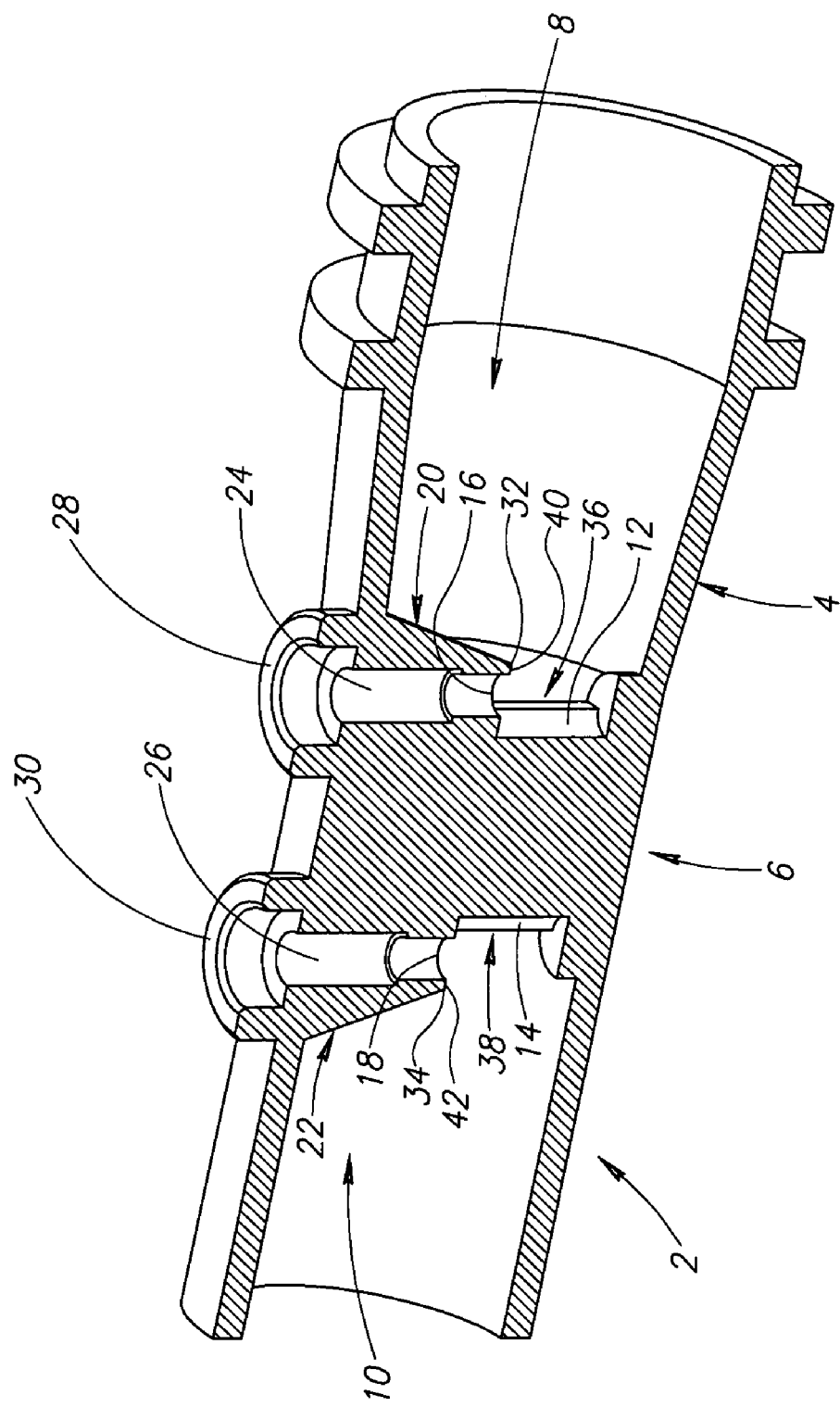
FIG. 1 is an illustration of the overall structure of the flow sensor.

FIG. 1 shows the overall structure of the current invention. The figure can best be understood by simultaneously referring to FIGS. 2, 3, and 4, which show side, top and short-axis views respectively of the device depicted in FIG. 1. A flow sensor 2 comprises a hollow cylindrical body 4 having a bore, and an interfering body 6 disposed within the bore of cylindrical body 4. In the preferred embodiment, cylindrical body 4 is a segment of respiratory tubing, although it will be understood that any form of tubing may be used without departing from the spirit of the current invention. In terms of the current invention, the word "tube" is hereby defined as referring to a hollow conduit of any cross-sectional shape, including circular, elliptical and square.

Figure 3:
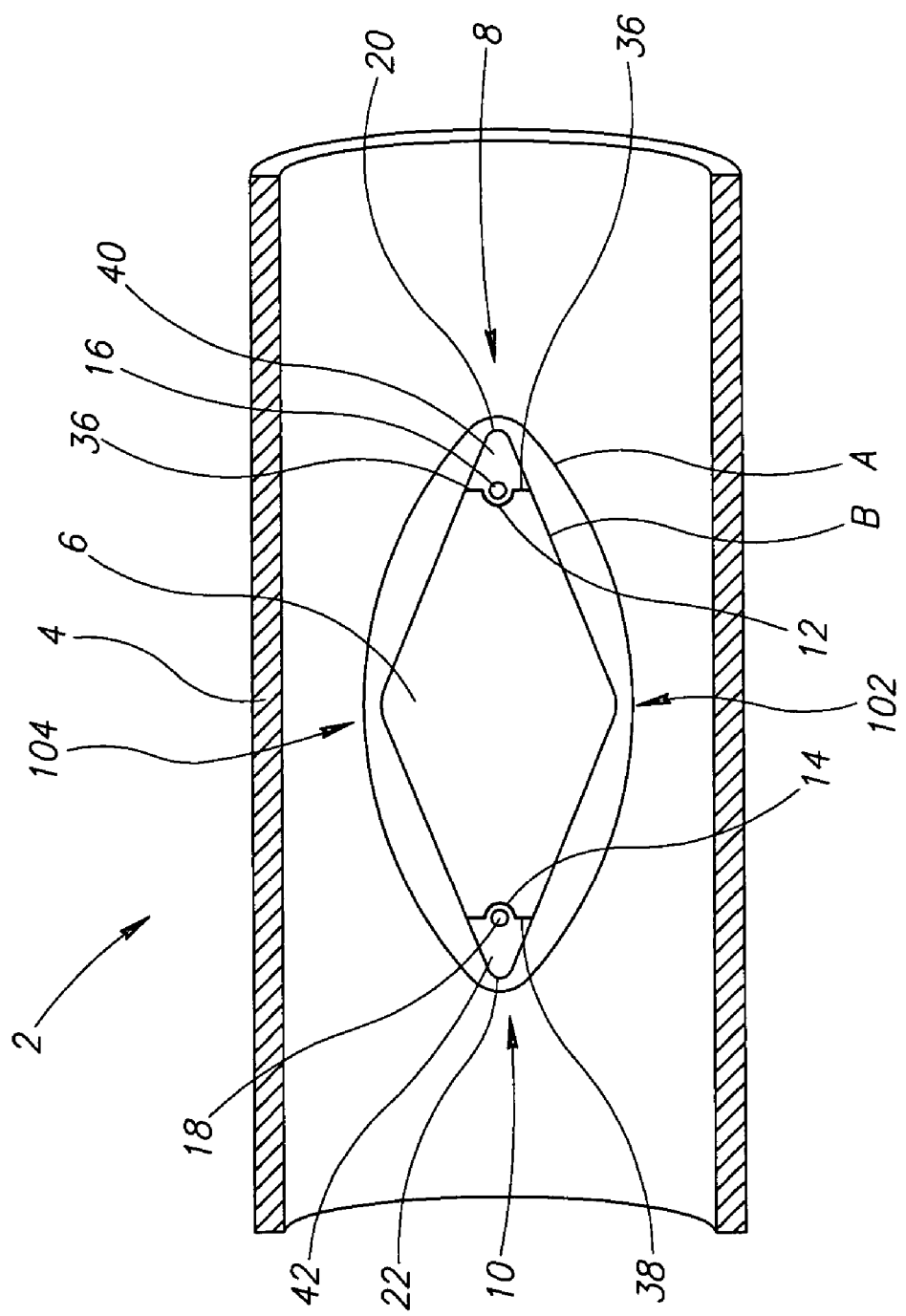
FIG. 3 is a longitudinal sectional top view of the flow sensor.

Interfering body 6 extends across the entire diameter of the bore of cylindrical body 4 and bisects the circular bore of cylindrical body 4. The width of interfering body 6 is less than the diameter of the bore of cylindrical body 4 and the longitudinal length of interfering body 6 is less than the length of the bore of cylindrical body 4. As can be seen in FIG. 3, the geometric cross section of the strut is symmetrical to the flow of respiratory gases flowing through sensor 2 in either direction, and when represented in two dimensions approximates a rhombus or ellipse in shape, as will be described below. As such, two corners of interfering body 6, at either end along its length, constitute longitudinally exposed edge portions 8 and 10 when represented in three dimensions. When airflow occurs through sensor 2, edge portions 8 and 10 are thus leading and trailing edges, depending on the direction of airflow. In addition, the two corners of interfering body 6 at either end along its width constitute lateral edges 102 and 104.

Figure 2:
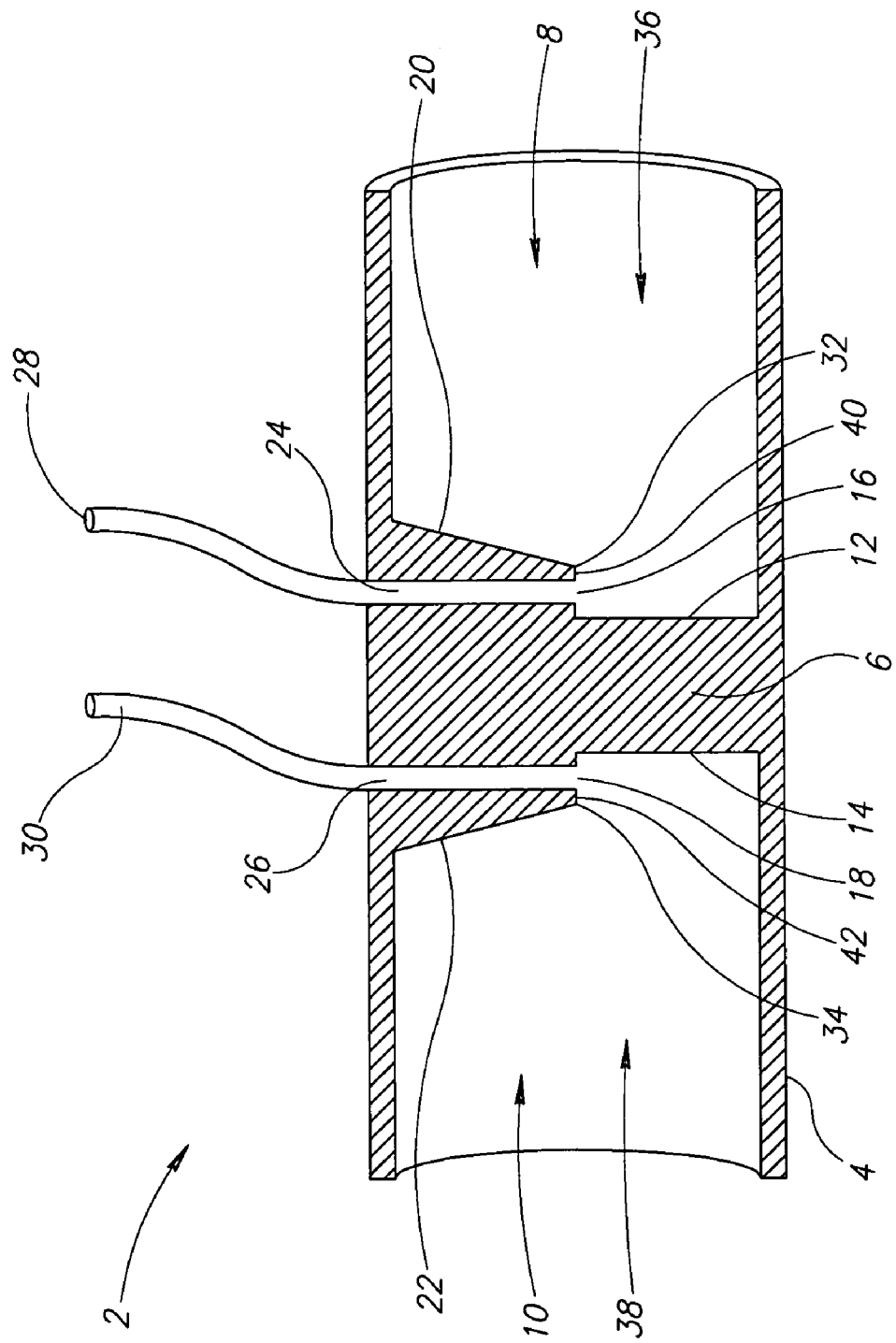
FIG. 2 is a longitudinal sectional side view of the flow sensor.

As can be seen in FIG. 2, interfering body 6 is wider superiorly, where it is in contact with the superior aspect of cylindrical body 4, than what it is inferiorly, where it is in contact with the inferior aspect of cylindrical body 4. Hereinafter, the wider, superior end of interfering body 6 will be referred to as the "base" of interfering body 6, and the narrower, inferior end will be referred to as the "inferior insertion" of interfering body 6.

A midpoint 32 bisects edge portion 8 into a first length 20, running from the base of interfering body 6 to midpoint 32, and a second length 36, running from midpoint 32 to the inferior insertion of interfering body 6. With regard to FIGS. 2 and 4, the term "horizontal" will refer to a plane that is parallel to the long axis of cylindrical body 4 and the term "vertical" will refer to a plane that is perpendicular to the long axis of cylindrical body 4. In a preferred embodiment, midpoint 32 is generally located at the mid-point of the vertical length of edge portion 8, that is, on the central axis of symmetry of cylindrical body 4. In an alternative embodiment, midpoint 32 may be located asymmetrically along the length of edge portion 8, that is, closer to one side of cylindrical body 4 than to the opposite side of cylindrical body 4, at essentially any location on edge portion 8. It is a particular feature of sensor 2 that first length 20 tapers at an incline from the inner surface of cylindrical body 4 towards midpoint 32. In a preferred embodiment, first length 20 is inclined at an angle of 13 degrees from the vertical plane, although other degrees of angulation may be used without departing from the spirit of the current invention. Second length 36, in contrast to first length 20, is oriented vertically, and is recessed into the body of interfering body 6 relative to first length 20. A semicircular groove 12 runs along the length of second length 36. A horizontal shelf 40, at the same vertical location on edge portion 8 as midpoint 32, lies between the medial end of first length 20 and semicircular groove 12. Horizontal shelf 40 contains a circular lumen 16 adjacent to semicircular groove 12. In a preferred embodiment, the diameter of circular lumen 16 is 1.54 mm. A bore 24 runs from circular lumen 16, within the body of interfering body 6 and in proximity to first length 20, to the outer surface of cylindrical body 4. At the outer surface of cylindrical body 4, bore 24 receives tubing 28. Tubing 28 runs from flow sensor 2 to a pressure transducer (not shown).

Figure 4:
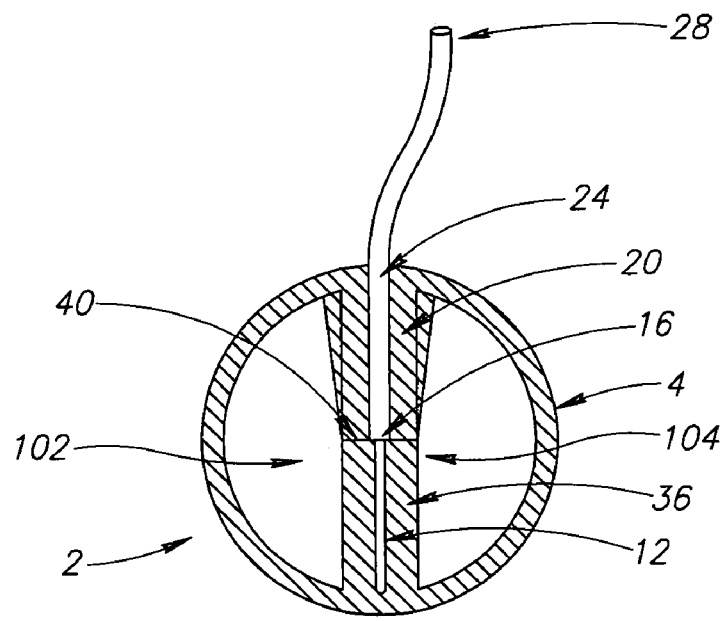
FIG. 4 is a short-axis view of the flow sensor.

As can be seen in FIG. 4, that part of lateral edge 102 which extends from the base of interfering body 6 to the vertical level of circular lumen 16 (hereinafter referred to as the "upper part" of lateral edge 102) tapers at an incline. In a preferred embodiment, this inclination is at an angle of 10 degrees from the vertical plane, although other degrees of angulation may be used without departing from the spirit of the current invention. In contrast, those parts of lateral edge 102 that extends from the vertical level of circular lumen 16 to the inferior insertion of interfering body 6 is oriented vertically. The dimensions and structure of lateral edge 104 are identical, in a mirror image, to those of lateral edge 102.

Edge portion 10 and its surrounding surfaces are essentially a mirror image of edge portion 8 and its surrounding surfaces. Thus a midpoint 34 bisects edge portion 10 into a first length 22 and a second length 38. First length 22 tapers at an incline (as described for edge portion 8) from the inner surface of cylindrical body 4 towards midpoint 34. Second length 38 is oriented vertically, and is recessed into the body of interfering body 6 relative to first length 22. A semicircular groove 14 runs along the length of second length 38. A horizontal shelf 42 lies between the medial end of first length 22 and semicircular groove 14. Horizontal shelf 42 contains a circular lumen 18 adjacent to semicircular groove 14. A bore 26 runs from circular lumen 18, within the body of interfering body 6 and in proximity to first length 22, to the outer surface of cylindrical body 4. At the outer surface of cylindrical body 4, bore 26 receives tubing 30. Tubing 30 runs from flow sensor 2 to a pressure transducer (not shown).

In a preferred embodiment of the current invention, the upper parts of lateral edges 102 and 104 (as depicted in FIG. 4) and first lengths 20 and 22 of edge portions 8 and 10 (as depicted in FIGS. 1 and 2) are straight. It is a particular feature of this embodiment, however, that in the upper part of interfering body 6 (that is, the part between the base of interfering body 6 and the vertical level of circular lumens 16 and 18), the external surfaces of interfering body 6 that lie between lateral edges 102 and 104 and edge portions 8 and 10, are not straight, but are concave in shape. Thus, the horizontal, geometric cross section of interfering body 6 changes, depending on the vertical level at which the cross section is depicted. As can be seen in FIG. 3, the horizontal cross-section of interfering body 6 at its base is essentially elliptical (indicated as contour "A" in FIG. 3), whereas the horizontal cross-section of interfering body 6 at the vertical level of circular lumens 16 and 18 approximates a rhombus with rounded corners (indicated as contour "B" in FIG. 3).

In a preferred embodiment, ellipse "A" has a circumference of 47.9 mm, a length of 17.7 mm, and a width of 6 mm, while contour "B" can be described as follows: the four corners of the rhombus-like shape are arcs of 3 mm diameter circles, and are connected to each other by tangents of those circles. The two circles whose arcs pass through edge portions 8 and 10 have a distance of 12 mm between their centers, and the two circles whose arcs pass through lateral edges 102 and 104 have a distance of 4 mm between their centers. The concave slopes of interfering body 6 have the effect of optimizing airflow patterns around interfering body 6 so as to prevent airflow turbulence from occurring in the flowing gas outside of the boundary layers. This configuration is particularly effective when cylindrical body 4 is fashioned in a Y-type configuration, as described below with regard to FIG. 6.

The upper part of interfering body 6 can thus be described as being a segment of an elliptically-based cone. This conical aspect of interfering body 6, whereby the sides of interfering body 6 slope inwards from the base of interfering body 6, is a novel feature of the current invention. When air flows through sensor 2, the inward sloping of the walls of interfering body 6 generates a pattern of airflow which characteristically includes a turbulent boundary layer around the base of interfering body 6. As will be well known to one familiar with the art, the interfering body of existing differential-pressure airflow sensors is designed so as to facilitate laminar airflow through the sensor, and specifically avoid turbulence. As such, the sides of the interfering body are essentially parallel to each other, a design feature that is aerodynamically advantageous for the purpose of minimizing turbulence both within and outside of the boundary layer of airflow. A point of novelty of the current invention lies in fashioning interfering body 6 with sloping (that is, non-parallel, or converging) sides so as to deliberately encourage turbulent airflow within sensor 2. This design feature results in an area of turbulent airflow within the boundary layer at the base of interfering body 6. As water precipitation is enhanced in turbulent (as opposed to laminar) boundary layers, droplets of water tend to precipitate at the base of interfering body 6, rather than in pressure-sensing circular lumen 16 (which is distant from the base of interfering body 6), thus preventing blockage of circular lumen 16 by water droplets formed by condensation. Although in a preferred embodiment of the current invention the surfaces of interfering body 6 are concave, it is envisaged that the surfaces of interfering body 6 may be of any shape, including being flat, without departing from the spirit of the current invention.

Sensor 2 functions as a differential-pressure flow sensor in an identical manner to that described for standard differential-pressure flow sensors, whereby static and dynamic pressures are sensed at edge portions 8 and 10 at either end of interfering body 6. It should be noted, however, that in terms of the functioning of the current invention, the actual points at which pressures are measured, using the venturi principle, are at circular lumens 16 and 18, which are distant from the inner surface of cylindrical body 4. Thus, accumulation of water on the inner surface of cylindrical body 4 does not cause obstruction of circular lumens 16 and 18, even if movement of the patient or of the respiratory tubing causes the accumulated water to flow within cylindrical body 4. It will be understood that circular lumens 16 and 18 on horizontal shelves 40 and 42 may be positioned at essentially any vertical displacement along edge portions 8 and 10 which would allow water to accumulate on the inner surface of cylindrical body 4 without obscuring circular lumens 16 and 18, without departing from the spirit of the current invention.

Figure 5:
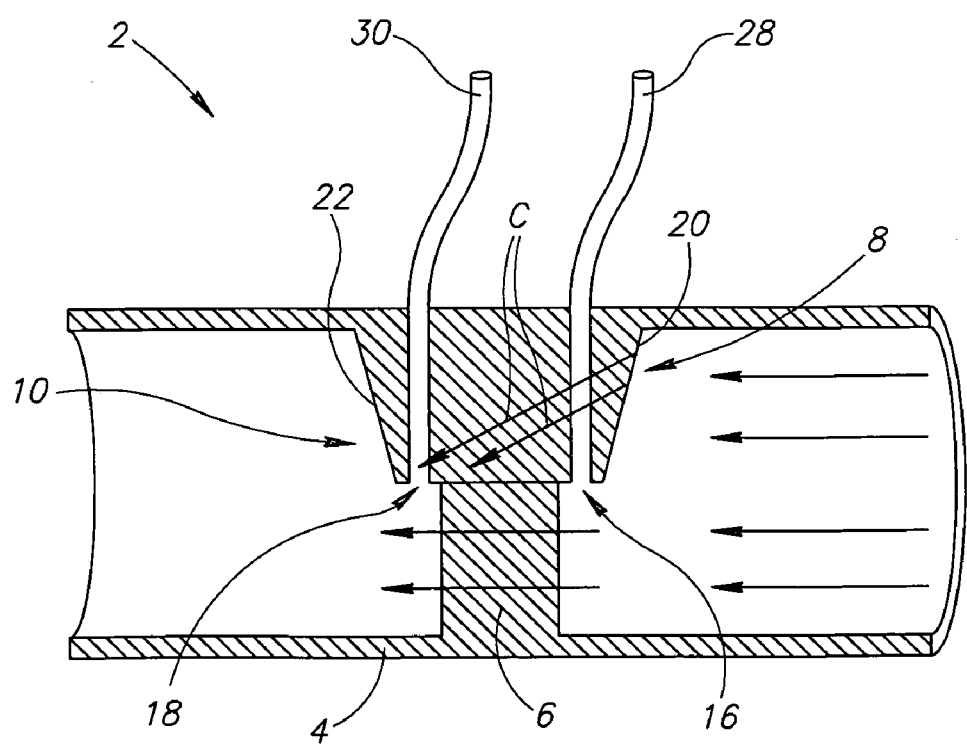
FIG. 5 is an illustration of airflow patterns caused by the leading edge of the interfering body.

FIG. 5 illustrates the pattern of airflow generated by edge portion 8. The inclination of edge portion 8 generates an airflow vector (indicated by the arrows marked "C") that is directed towards circular lumen 18. This is in contrast to existing differential-pressure flow sensors, in which the leading edge portion is vertical and is not designed to specifically create a flow vector directed at the opposite pressure-sensing port. In the current invention, airflow along this vector has the effect of "flushing" water droplets out of circular lumen 18. It will be understood that edge portions 8 and 10 may be fashioned in essentially any manner that produces an airflow vector directed towards circular lumens 18 and 16 respectively, without departing from the spirit of the current invention.

Figure 6:
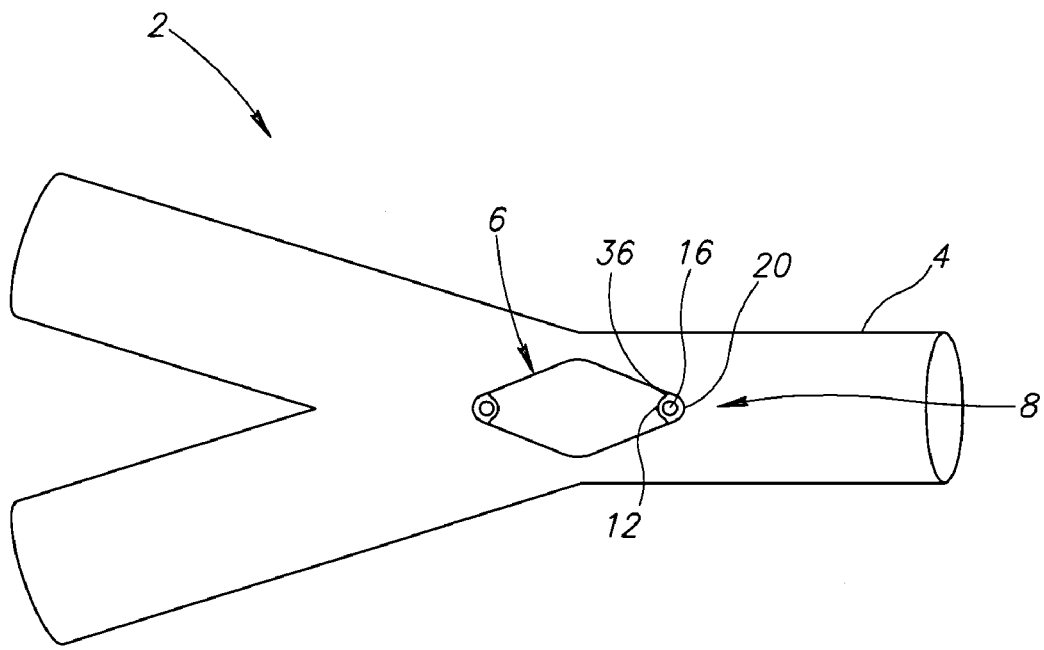
FIG. 6 is an illustration of a preferred embodiment of the flow sensor.

In a preferred embodiment, as shown in FIG. 6, cylindrical body 4 is fashioned in a Y-type configuration, such that interfering body 6 is positioned at the junction of the limbs of the Y, each of the two proximal limbs being functional to convey either inspiratory or expiratory airflow only, and the single distal limb being functional to convey bi-directional airflow to and from the patient interface. In an alternative embodiment, as shown in FIG. 1, cylindrical body 4 is executed in a straight cylinder configuration.

Figure 7:
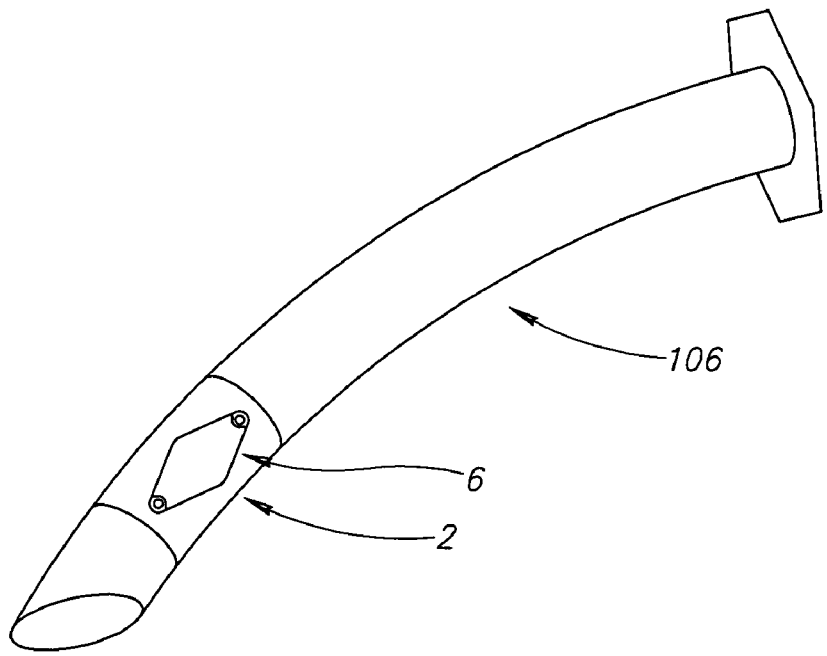
FIG. 7 is an illustration of an alternative embodiment of the flow sensor.

It should be noted that flow sensor 2 may be located at essentially any point along the path of airflow of a patient, whether such point be within the patient's respiratory tract, within the tubing of a ventilator connected to a patient, within a ventilator itself, or within essentially any device which receives either positive-pressure or negative-pressure airflow from a patient. In particular, as shown in FIG. 7, flow sensor 2 may be located at the distal end of an endotracheal tube 106. Similarly, it is envisaged that flow sensor 2 may be located in a tracheostomy cannula, a suction catheter, a bronchoscope, or any other instrument that may be inserted into the respiratory tract.

Figure 8:
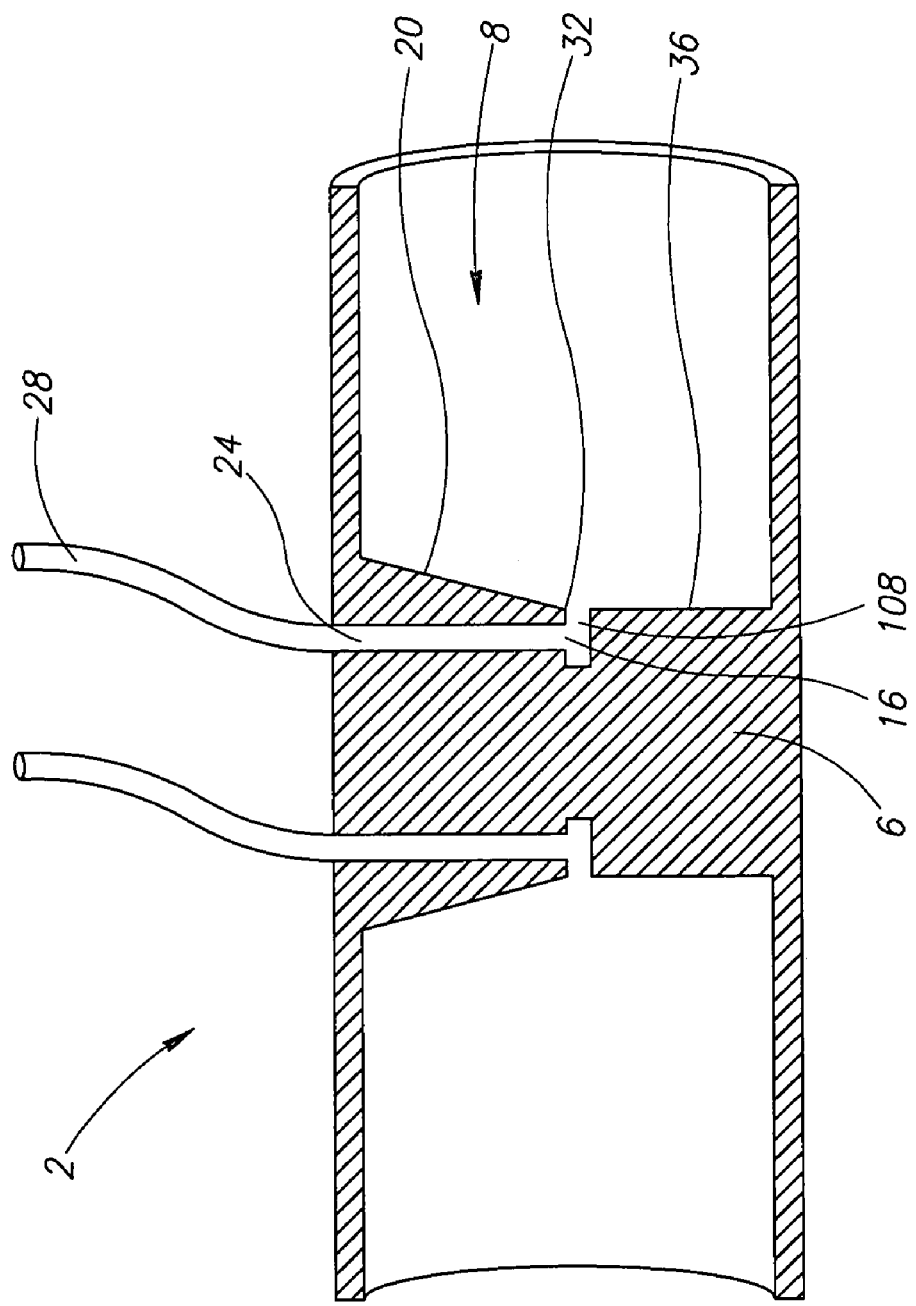
FIG. 8 is an illustration of an alternative embodiment of the flow sensor.

FIG. 8 illustrates an alternative embodiment of interfering body 6, wherein second length 36 is not recessed in relation to first length 20. In this embodiment, circular lumen 16 opens into a recess 108 within second length 36 (rather than opening onto shelf 40 as in the preferred embodiment of interfering body 6 illustrated in FIGS. 1 through 6). As such, circular lumen 16 is located within interfering body 6, rather than on edge portion 8 of interfering body 6. Thus in both embodiments circular lumen 16 is located in edge portion 8: either recessed within edge portion 8 or disposed upon edge portion 8.

Although the current invention has been described as a ventilatory airflow sensor, it is envisaged that the current invention may be used in any application, both within and without the field of medicine, wherein the measurement of humid gas flow may be desirable.

There has therefore been described a differential-pressure flow sensor that, without the use of electrical components in the sensor, prevents condensation of water vapor in the pressure-sensing lumens of the sensor and prevents blockage of the pressure-sensing lumens by condensed water within the respiratory tubing.

While the present invention has been described with reference to one or more specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

What is claimed is:

1. A respiratory tract differential-pressure flow sensor, comprising:
    a tube having a distal end that is insertable into a respiratory tract;
    an interfering body disposed within said tube proximal to said distal end and having a first edge facing one end of said tube and a second edge facing away from said end, said interfering body extending across the diameter of said tube;
    a first pressure sensing port operative to sense an air pressure, said first port being disposed in said first edge not abutting the wall of said tube; and
    a second pressure sensing port operative to sense an air pressure, said second port being disposed in said second edge not abutting the wall of said tube,
    wherein either of said edges is inclined inwardly towards the axis of said interfering body extending across said diameter of said tube.

* * * * *